(12) United States Patent
Fountain et al.

(10) Patent No.: US 11,446,183 B2
(45) Date of Patent: Sep. 20, 2022

(54) EAR COVER ASSEMBLY

(71) Applicant: LOUD AND CLEAR SAFETY PTY LTD, Harkaway (AU)

(72) Inventors: Peter David Fountain, Harkaway (AU); Jack Magree, North Melbourne (AU)

(73) Assignee: LOUD AND CLEAR SAFETY PTY LTD, Harkaway (AU)

( * ) Notice: Subject to any disclaimer, the term of this patent is extended or adjusted under 35 U.S.C. 154(b) by 176 days.

(21) Appl. No.: 16/607,986

(22) PCT Filed: Apr. 24, 2018

(86) PCT No.: PCT/AU2018/050372
§ 371 (c)(1),
(2) Date: Oct. 24, 2019

(87) PCT Pub. No.: WO2018/195592
PCT Pub. Date: Nov. 1, 2018

(65) Prior Publication Data
US 2021/0106466 A1    Apr. 15, 2021

(30) Foreign Application Priority Data
Apr. 24, 2017   (AU) ............................... 2017901486

(51) Int. Cl.
*A61F 11/14* (2006.01)
*A61F 9/02* (2006.01)
(52) U.S. Cl.
CPC ............. *A61F 11/14* (2013.01); *A61F 9/025* (2013.01); *A61F 9/029* (2013.01); *A61F 2210/0076* (2013.01)

(58) Field of Classification Search
CPC ........... A61F 11/14; A61F 9/025; A61F 9/029
(Continued)

(56) References Cited

U.S. PATENT DOCUMENTS 4,856,089 A    8/1989  Horton
5,133,596 A *  7/1992  Korny ................... G02C 11/00
                                                    351/158
(Continued)

FOREIGN PATENT DOCUMENTS

EP     0353930 A1    2/1990
GB     2209923 A     6/1989
(Continued)

OTHER PUBLICATIONS

Notification of Transmittal of International Preliminary Report on Patentability dated Apr. 8, 2019, (22 pages).
(Continued)

*Primary Examiner* — F Griffin Hall
(74) *Attorney, Agent, or Firm* — Maschoff Brennan

(57) ABSTRACT

An ear cover assembly having a resilient frame attached to ear covers via a rotatable mounting located in an upper portion of the ear cover, the resilient frame being configured to apply clamping force to hold the ear covers in place over the wearer's ears and the geometry of the frame and rotational mounting being configured to distribute clamping force over the ear cover to hold the assembly in place when worn. Thus, the ear cover assembly can be supported in place by the rotationally mounted frame rather than a headband. The frame can be used to support elements such as eye protectors, visors, face masks, microphone etc.

20 Claims, 11 Drawing Sheets

(58) Field of Classification Search
USPC .............................................. 2/209; 128/866
See application file for complete search history.

(56) References Cited

U.S. PATENT DOCUMENTS

| | | | |
|---|---|---|---|
| 5,353,071 A | 10/1994 | Bradshaw | |
| 5,724,119 A | 3/1998 | Leight | |
| 7,020,901 B2 | 4/2006 | Brhel | |
| 2004/0181841 A1 | 9/2004 | Artzberger | |
| 2005/0015852 A1 | 1/2005 | Brhel | |
| 2011/0194029 A1 | 8/2011 | Herrmann et al. | |
| 2011/0209273 A1* | 9/2011 | Fountain | A61F 11/14 2/423 |
| 2012/0272484 A1 | 11/2012 | Willborn | |
| 2013/0278886 A1 | 10/2013 | Vollet | |
| 2016/0199228 A1 | 7/2016 | Haukap | |
| 2018/0252938 A1* | 9/2018 | Thorsell | G02C 5/10 |

FOREIGN PATENT DOCUMENTS

| | | |
|---|---|---|
| WO | 1998007062 A1 | 2/1998 |
| WO | 2010022440 A1 | 3/2010 |
| WO | 2013075166 A1 | 5/2013 |

OTHER PUBLICATIONS

International Search Report dated Jul. 16, 2018, (4 pages).
Extended European Search Report dated Nov. 11, 2020, in related PCT Application No. PCT/AU2018/050372.
Patent Examination Report dated May 18, 2021 in related New Zealand Application No. 759189.

\* cited by examiner

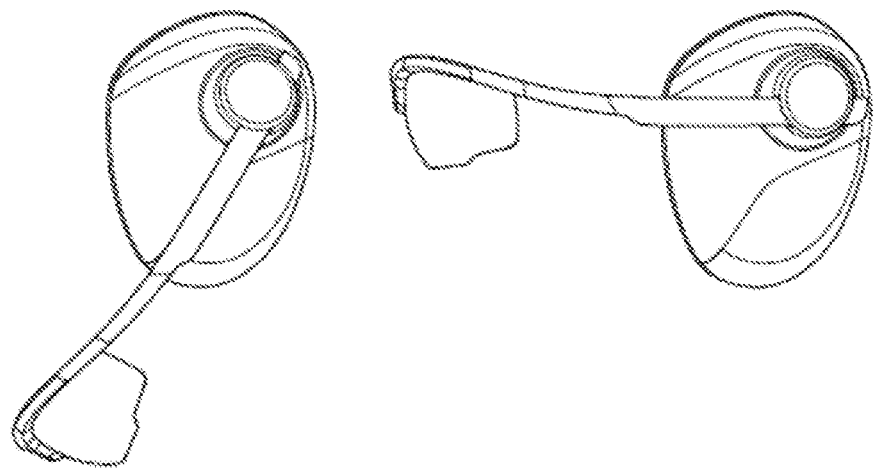
Figure 3a    Figure 3b
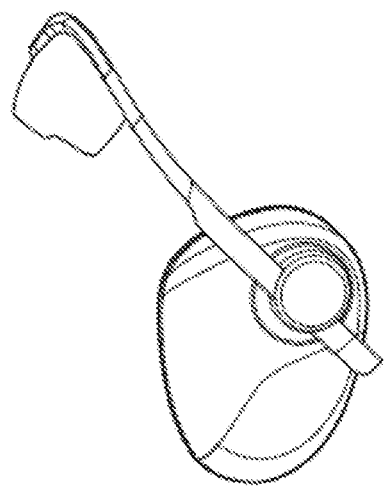 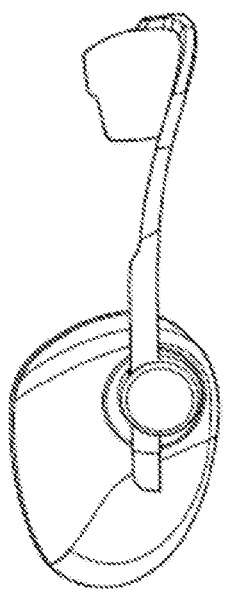
Figure 3c    Figure 3d

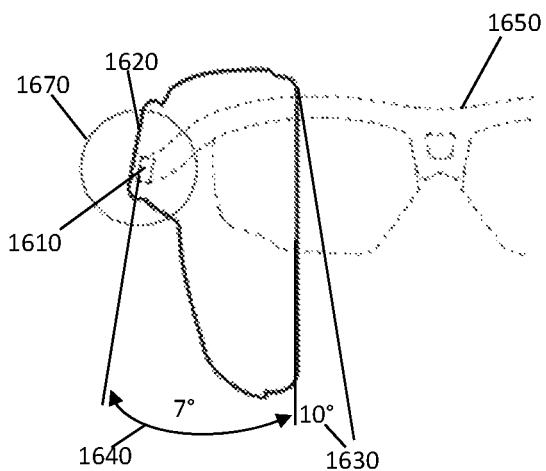
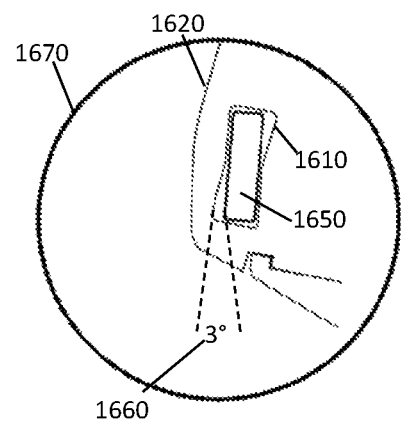
Figure 16a              Figure 16b
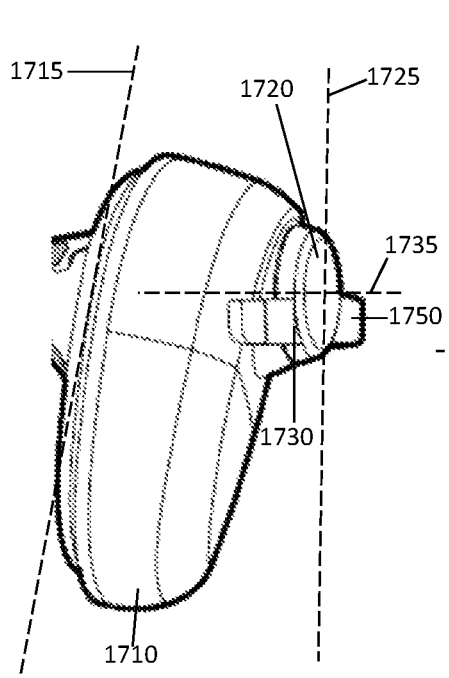
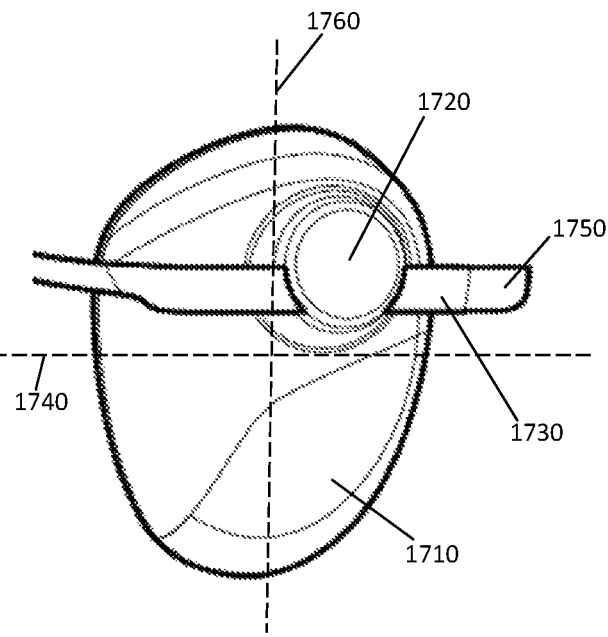
Figure 17a              Figure 17b

EAR COVER ASSEMBLY

FIELD OF THE INVENTION

The field of the invention is an assembly for eye and ear covers that can support ear covers on a wearer's head without need of a head band and also support an eye cover. Applications of the assembly include safety ear and eye protection or consumer products combining ear and eye covers.

BACKGROUND OF THE INVENTION

Eye protection safety equipment such as safety goggles or visors are known. Such devices provide a barrier in front of the wearer's eyes for protection against flying particles or liquid splashes. Typically, the barrier will be transparent or semi-transparent to enable the wearer to see through the barrier. Known hearing protection safety equipment includes ear muffs or ear plugs which are worn to dampen or muffle sounds to minimise hearing damage which may occur from being exposed to a noisy environment. Ear muff style ear protectors can provide more effective hearing protection than ear plugs and are therefore preferred for many environments. In some workplaces it is mandatory to wear safety equipment such as eye protection, ear protection, and head protection.

A problem with ear muffs is that the seal around the wearer's ear made by the sound protective padding if the muff will be broken when worn with safety glasses or even regular spectacles, thus reducing the sound protection provided. Further ear muffs are typically held in place by a headband, which can interfere with headwear, such as safety head protection. This problem is overcome for some uses by providing hard hats with attached ear muffs and in some instances also safety visors. However, this is an all in one device giving "all or nothing" protection, as when the wearer removed their helmet they also remove the hearing protection and sight protection. There may also be some instances where hard hat protection is not required or desirable, but other headwear would be useful, for example mowing lawns in the open sun one would typically prefer to wear a hat that provides sun protection and is cooler than a hard hat.

It is desirable for safety equipment to be practical and comfortable. A solution that has been proposed is to provide a combined eye and ear protection apparatus where the eye protection is mounted to the ear muffs. Some such proposed devices include a headband to help support the device on the wearer's head, which can interfere with headwear. Other proposed solutions use tension from the eye protection to hold the device in place on the wearer's head. The tension required to be provided through the eye protection to clamp the ear muffs on the wearer's ears and hold these in place without use of a headband can be difficult to achieve. So, to date, traditional headband or helmet mounted ear covers are typically used.

SUMMARY OF THE INVENTION

According to a first aspect there is provided an ear cover assembly comprising:
two ear covers, each ear cover having a rotatable mounting located in a mounting position offset from the centre of the ear cover;
a resilient frame comprising a right end portion, a central portion, and a left end portion,
each of the right end portion and the left end portion being configured to attach to a respective one of the ear covers via the rotatable mounting,
the central portion being configured to orient the right end portion and the left end portion to hold ear covers opposite one another for placement in use to cover a wearer's ears, and to support an assembly for positioning in front of a wearer's face,
the resilient frame being configured to apply clamping force to urge the ear covers inwardly to hold the assembly in place on the wearers head;
the rotational mounting being configured to limit relative movement between the frame and ear cover in a direction perpendicular to a main axis of rotation of the mounting, and
the relative geometry of the frame and rotational mounting being configured to distribute clamping force over the ear cover to compensate for the offset mounting position.

In an embodiment the relative geometry of the frame and rotational mounting applies a twisting force. The twisting force can be provided by the frame resilience, and angular orientation of left end portion and right end portion within the respective rotational mountings when worn. In an embodiment each respective rotational mounting can be configured to hold the respective left end portion and right end portion such that for any rotational orientation the respective left end portion and right end portion retained within the mounting is angled relative to the centre of the ear cover such that the most central part is angled outwardly of centre of the ear cover relative to the least central part of the respective left end portion and right end portion retained within the mounting to thereby cause the twisting force when worn.

In an embodiment each rotational mounting is oriented such that the plane of rotation is angled relative to a plane through ear contacting surfaces of the ear cover and includes a channel for receiving the respective left end portion and right end portion, the channel being offset from the main axis of rotation of the mounting in a direction toward the ear cover centre, wherein the left end portion and right end portion are configured to engage with one or more surfaces within the channel, the surfaces within the channel being configured such that in a rotational position where the channel is substantially perpendicular to a meridian line though the centre of the ear cover the surfaces cause longitudinal twisting of the respective end portion to cause the twisting force when worn, and in a rotation position where the channel is substantially parallel to the meridian line through the centre of the ear cover the surfaces cause longitudinal flexing of the respective left end portion and right end portion due to the angle of the channel relative to the plane through ear contacting surfaces of the ear cover to provide the twisting force when worn. In some embodiments the left end portion and right end portion have a planar portion to engage with the surfaces within the rotation mounting.

In some embodiments of the ear cover assembly the assembly supported by the frame is an eye cover assembly.

In some embodiments of the ear cover assembly the assembly supported by the frame is a microphone.

In some embodiments the rotational mounting for each ear cover comprises a rotational mounting socket in a fixed position in the upper portion of the ear cover, and one or more rotational assembly components to be received in the socket to form a rotational plug including the channel, and wherein the socket is oriented such that the plane of rotation of the plug is angled relative to a plane through ear contacting surfaces of the ear cover.

The two ear covers can be asymmetrical and comprise a left ear cover and a right ear cover, with the socket of each ear cover oriented such that the plane of rotation of the plug is angled relative to a plane through ear contacting surfaces of the ear cover allowing an identical plug to be used for assembling the rotational mounting for each of the left and right ear covers.

In some embodiments of the ear cover assembly the frame comprises a resilient skeleton spanning the right end portion, central portion and left end portion of the frame and providing resilience to apply the clamping force. For example, the resilient skeleton can be an elongate curved band and being substantially flat through the left end portion and right end portion. The band may be formed of resilient metal. Alternatively, the band can have a composite structure comprising one or more layers of resilient material in a laminate structure. Alternatively, the resilient skeleton may be formed of a plastic material. The plastic material having sufficient strength and resilience.

The frame can further comprise a non-metallic coating. In some embodiments the non-metallic coating increases the resilience of the frame.

The frame of some embodiments can further comprise a non resilient eye cover assembly mounting configured to mount an eye cover assembly to the central portion.

The ear cover assembly of any embodiment as described above can be further configured to allow adjustment of the position of each ear cover along the respective left end portion or right end portion. In some embodiments the rotational mounting is configured with a channel to allow sliding of the rotational mounting along the respective left end portion or right end portion. In some embodiments the left end portion and right end portion of the frame further comprise a ratchet portion and the rotational mounting is configured to engage with the ratchet portion provided on the respective left end portion and right end portion to inhibit unintentional sliding of the rotational mounting along the respective left end portion or right end portion. In some alternative embodiments surface friction between the rotational mounting and the respective left end portion or right end portion of the frame inhibits unintentional sliding of the rotational mounting along the respective left end portion or right end portion.

In some embodiments the ear covers are ear muffs style ear protectors configured to provide hearing protection for the wearer. In an example each ear protector comprises an inner sound insulating portion adapted to rest against and substantially or entirely cover the outer ear of a wearer; and an outer shell made of rigid material and attached to the inner insulating portion, wherein the rotational mounting is attached to the outer shell of the ear protector. In some embodiments the outer shell has a removable portion adapted to be selectively removed and replaced whereby when removed an aperture is formed in the outer shell. In some embodiments sound insulating qualities of the ear protector can be adjusted by adding or removing additional sound insulating material via the aperture in the outer shell.

In some embodiments at least one ear cover includes an electronic device comprising a wireless receiver and speaker. For example, the ear covers can be configured as pair of headphones. In an embodiment the ear covers are configured as left and right stereo headphones.

The ear cover assembly can further comprise an eye cover assembly wherein the eye cover assembly comprises an eye protection assembly. For example, the eye protection assembly can be configured as any one of safety glasses, safety visor or mask. Other alternatives are also contemplated.

In an alternative embodiment the eye cover assembly is configured for sunglasses.

The eye cover assembly can be configured to include vision corrective lenses. In an embodiment the eye cover assembly is configured to enable removable attachment of vision corrective lenses. In another embodiment the eye cover assembly incudes integrated vision corrective lenses.

The eye cover assembly can be removably attached to the frame.

In an embodiment the ear cover assembly further comprises a microphone assembly. In an embodiment the microphone assembly comprises a microphone mounted on a stem for positioning the microphone proximate a wearer's mouth, the stem being attached to one of the ear covers via a second rotational mounting.

According to a second there is provided an ear cover assembly comprising:
  two ear covers, each ear cover having a rotatable mounting;
  a resilient frame comprising a right end portion, a central portion, and a left end portion,
    each of the right end portion and the left end portion being configured to attach to a respective one of the ear covers via the rotatable mounting,
    the central portion being configured to orient the right end portion and the left end portion to hold ear covers opposite one another for placement in use to cover a wearer's ears, and to support an assembly for positioning in front of a wearer's face,
    the resilient frame being configured to apply clamping force to urge the ear covers inwardly to hold the assembly in place on the wearers head;
  the rotational mounting being configured to limit relative movement between the frame and ear cover in a direction perpendicular to a main axis of rotation of the mounting, and
  the relative geometry of the frame and rotational mounting being configured to alter the clamping force applied by the frame based on the rotational position of the frame.

According to a third aspect there is provided an ear cover assembly comprising:
  one ear cover having a rotatable mounting;
  a head contacting support having a rotatable mounting; and
  a resilient frame comprising a right end portion, a central portion, and a left end portion,
    each of the right end portion and the left end portion being configured to attach to a respective one of the ear covers and support via the rotatable mounting,
    the central portion being configured to orient the right end portion and the left end portion to hold the ear cover and the support substantially opposite one another for placement in use with the ear cover covering one of the wearer's ears and with the head contacting support against the wearers head near their other ear, and to support an assembly for positioning in front of a wearer's face,
    the resilient frame being configured to apply clamping force to urge the ear cover and head contacting support inwardly to hold the assembly in place on the wearers head;
  the rotational mounting being configured to limit relative movement between the frame and respective ear cover and head contacting support in a direction perpendicular to a main axis of rotation of the mounting, and
the relative geometry of the frame and rotational mounting being configured to alter the clamping force applied by the frame based on the rotational position of the frame.

BRIEF DESCRIPTION OF THE DRAWINGS

An embodiment, incorporating all aspects of the invention, will now be described by way of example only with reference to the accompanying drawings in which:

FIGS. 3a to 3d illustrate range of movement of the eye cover frame relative to the ear covers;

FIGS. 16a and 16b illustrate channel for retaining the frame end in an embodiment of the ear cover assembly;

FIGS. 17a and 17b illustrate geometry of the ear cover and rotational mounting in accordance with an embodiment of the invention;

DETAILED DESCRIPTION

An aspect of the present invention provides an ear cover assembly having a resilient frame attached to ear covers via a rotatable mounting located in an upper portion of the ear cover, the resilient frame being configured to apply clamping force to hold the ear covers in place over the wearer's ears and the geometry of the frame and rotational mounting being configured to distribute clamping force over the ear cover to hold the assembly in place when worn. Thus, the ear cover assembly can be supported in place by the rotationally mounted frame rather than a headband. For example, in an embodiment the frame is a band supporting safety glasses, the band supporting both the safety glasses and ear covers when worn. This embodiment does not have a headband and therefore can be worn with a variety or headwear such as hard hats, broad brimmed sun hats, caps etc. In another embodiment the frame can support sunglasses. The ear covers may be any type of ear covers such as, hearing protective ear muffs, headphones, headsets, thermal protective ear muffs etc.

Figure 1:
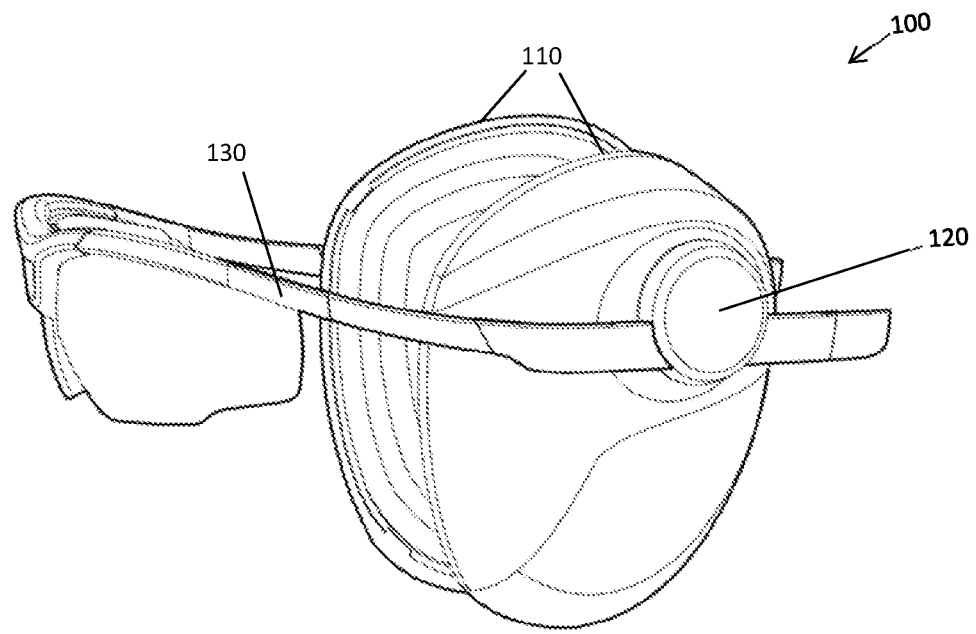
FIG. 1 shows an example of a combined eye and ear protection device in accordance with an embodiment of the present invention.

An embodiment of the ear cover assembly is illustrated in FIG. 1 and a variety of views are shown in FIGS. 2a to 2d. The ear cover assembly 100 comprises two ear covers 110, each ear cover having a rotatable mounting 120 located in an upper portion of the ear cover 110, and a resilient frame 130 comprising a right end portion 220, a central portion 210, and a left end portion 230. Each of the right end portion 220 and the left end portion 230 are configured to attach to a respective one of the ear covers 240, 250 via the rotatable mounting 120. The central portion 210 is configured to orient the right end portion 220 and the left end portion 230 to hold ear covers 240, 250 opposite one another for placement in use to cover a wearer's ears, and to support an eye cover assembly 260. The resilient frame 130 is configured to apply clamping force to urge the ear covers 240, 250 inwardly to hold the assembly in place on the wearers head. The rotational mounting 120 is configured to limit relative movement between the frame 130 and ear cover 240, 250 in a direction perpendicular to a main axis of rotation of the mounting, and the relative geometry of the frame 130 and rotational mounting 110 being configured to distribute clamping force over the ear cover.

The applicants had previously devised a combined ear and eye protection apparatus having ear muff style protectors which are held in place on the wearer's head by tension provided through an eye protector assembly, without need of a supporting headband. A comprehensive description of the applicant's original combined hearing and eye protection device can be found in international patent application publication number WO 2010/022440, the disclosure of which is incorporated in the present specification by reference. An advantage of the applicant's device design is the eye protector assembly, is connected to the two ear muff ear protectors using a mounting located toward an upper edge of the ear protector. This means that when worn each connection between the ear protector and eye protector assembly will be positioned relative to the wearer's ear toward the top or above the wearer's ear. This high pivot mounting position provides a number of advantages including any one or more of:

allowing an ear protector to be swung away from the wearer's ear without disturbing the eye protection,
easy rotation of the eye protector away from the wearer's eyes (for example to the top of their head) without disturbing the ear protection,
ergonomic design allowing the eye protector assembly to be shaped more like regular safety glasses and/or enable regular spectacles to be more easily worn with the device, and a large portion of the ear protector cover is exposed enabling this space to be utilised for other things such as advertising or an aperture for changing the ear cover configuration—such as adding further insulation or a device such as a Bluetooth earpiece.

The idea of a combined self-supporting ear and eye protection apparatus without a headband had been previously proposed where the rotational mounting for the eye protection or visor was centrally located over the ear protector. This is because a central mounting will distribute clamping force evenly over the ear protector to hold this in place on the wearer's ear. Moving the mounting point to an upper portion of the ear protector device presents a technical problem, this being to distribute the clamping force effectively over the ear cover to support the apparatus in place without needing a supporting headband.

Figures 4A, 4B:
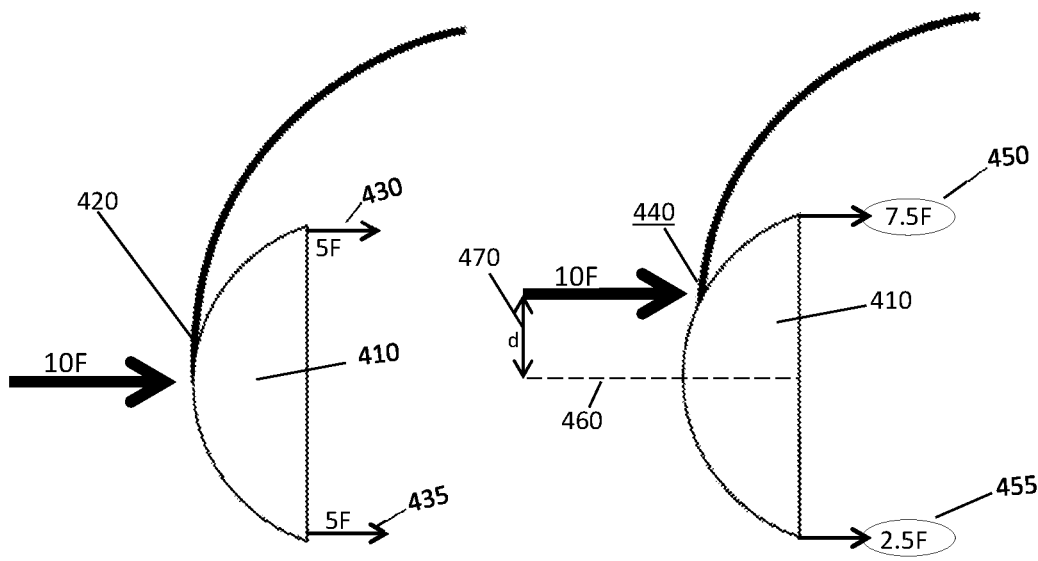
FIGS. 4a and 4b illustrate the difference in force application for a mounting located centrally for an ear cover 4a and for a mounting located in a upper portion of an ear cover 4b.
Figure 5:
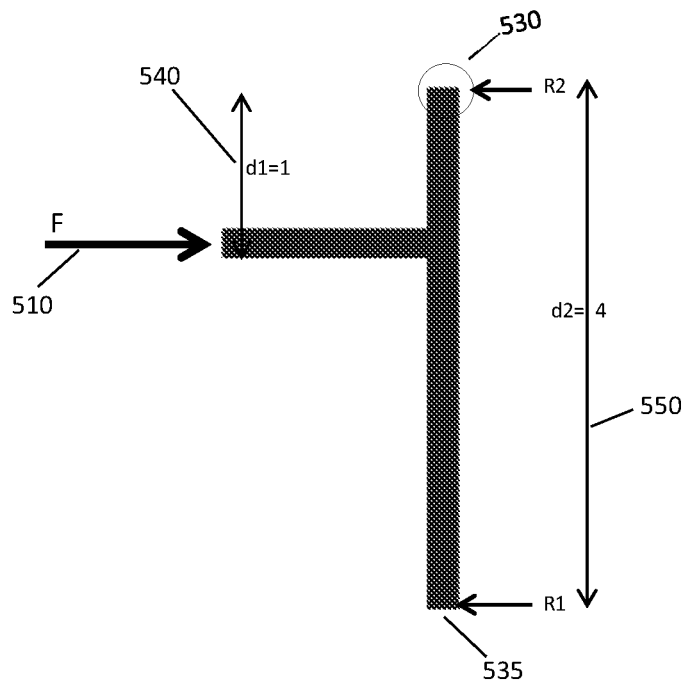
FIG. 5 illustrates the force distribution problem is a side view of a person wearing the ear and eye protection apparatus of FIG. 1 illustrating the eye protector raised.

FIG. 4a schematically illustrates an embodiment of an ear cover 410 having a centrally located mounting 420, for example as is common with an overhead supporting headband. Forces from the band are applied at the centre of the ear cover which results in even force distribution. Point clamping force (10 F) applied to the centrally located mounting point 420 is distributed evenly over the ear cover 410 so the force at the top of the ear cover 430 (5 F) is equivalent to the force at the bottom of the ear cover 435 (5 f). This is due to the symmetry of the ear cover about the point 420 where the clamping force is applied. However, when the mounting point for a rotational mounting is not central to the ear cover, a force (i.e. clamping force) applied to a point ceases to be evenly distributed over the ear cover. FIG. 4b illustrates the problem where using an off-centre mounted band (high pivot point) 440 the force is applied off-centre, resulting in uneven force distribution. The mounting 440 is offset from the centre of the ear cover 460 by a distance d 470. Due to the off-centre mounting 440 causing uneven force (10 F) distribution, stronger clamp force (7.5 F) is applied at the upper portion 450 than the lower portion 455 (2.5 F) of the ear cover 410. The difference in apparent force at the upper portion 450 and lower portion 455 of the ear cover 410 will depend on the position of the mounting 440 relative to the centre 460 of the ear cover 410. As illustrated in FIG. 5, the force distribution problem can be represented by a line 505 through the ear cover from a top edge the 530 to a bottom edge 535, and a point 520 along this line 505 representing the mounting position and therefore the point 520 at which clamping force 510 from the band is applied, this clamping force being distributed along the line 505. The force application point 520 is located at a distance d1 540 from the top edge 530 and the distance between the top 530 and bottom 535 edge is d2 550. The force distribution can be calculated:

$$F \times d1 = R1 \times d2 \qquad \text{[Equation 1]}$$

Where F is the applied point force, d1 is the distance from the force application point 520 to the top edge 530, d2 is the distance between the top edge 530 and the bottom edge 535, and R1 is the reactive force at the bottom edge 535. The force is distributed based on the distance from the point of force application. Where d1=1 and d2=4 the force at the respective ends is calculated:

$$R1 = \frac{d1}{d2}F = \frac{1}{4}F \qquad \text{[Equation 2]}$$

$$R2 = \frac{d2-d1}{d2}F = \frac{3}{4}F \qquad \text{[Equation 3]}$$

Thus, force at the top edge 530 is R2=7.5 F and the force at the bottom edge 535 is R1=2.5 F. Illustrating that off-centre application of force due to the high mounting point gives uneven clam pressure.

To compensate for the uneven clamp force due to the high mounting position the geometry of the frame and rotational mounting is configured to distribute clamping force over the ear cover. In embodiments the rotational mounting is configured to limit relative movement between the frame and ear cover in a direction perpendicular to a main axis of rotation of the mounting, and the relative geometry of the frame and rotational mounting being configured to distribute clamping force over the ear cover.

Figure 6:
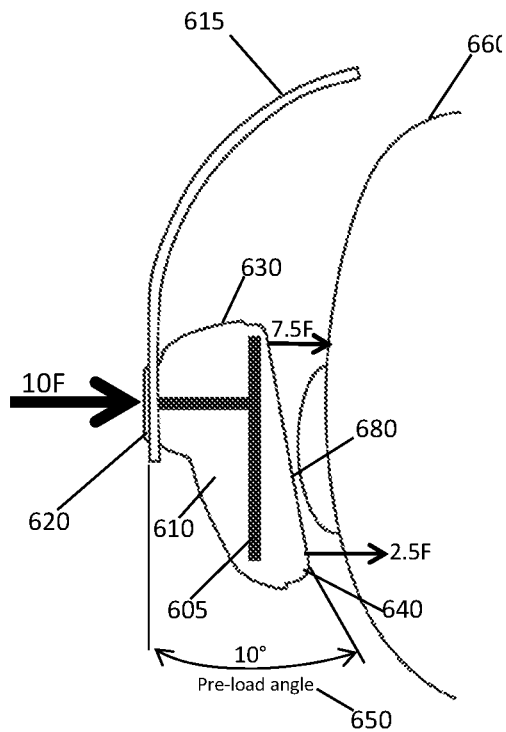
FIG. 6 shows an ear cover in an initial (rest) position.
Figure 7:
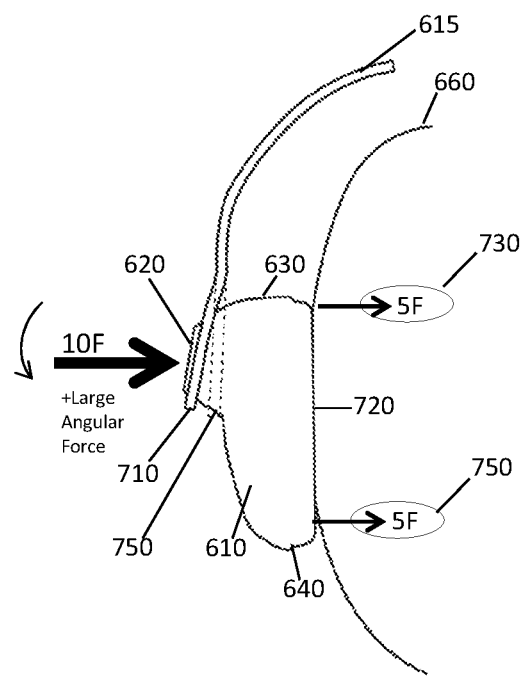
FIG. 7 shows the ear cover of FIG. 6 in position on a wearer's head.

In an embodiment the frame is configured to apply a twisting force to the ear cover to provide additional clamping force at the lower end of the ear cover. In such embodiments the resilience of the frame is utilised to apply an angular force to ear cover to increase the force applied to urge the lower portion of the ear cover inwardly to the wearer's head. An embodiment is illustrated in FIG. 6 where the ear cover 610 in an initial (rest) position is held by the geometry of the fame 615 and rotational mounting 620 at an angle where the lower edge of the ear cover 640 will be further inward towards the wearer's head 660 than the top of the ear cover 630, so the side 680 of the ear cover 610 that will contact the wearer's head 660 is held at an angle 650 relative to the line 605 used for modelling point force distribution. Further in this embodiment the rotational mounting 620 is configured to hold the end of the frame 615 retained within the mounting in a substantially fixed position in a rotating portion of the mounting, to thereby limit relative angular movement between the ear cover and the frame perpendicular to axis of rotation. By holding the frame and rotational portion of the mounting in relatively fixed position the frame can apply angular force to the ear cover once in position on a wearer's head 660, for example as shown in FIG. 7. FIG. 7 shows the ear cover 610 of FIG. 6 in position on a wearer's head 660. In FIG. 7 the frame 615 is flexed outwardly 710 from the rest position 750 and therefore applies an angular force to increase the force 740 applied at the lower edge 640 of the ear cover. This combination of frame clamping force and the additional twist force can create an even clamp force over the side 720 of the ear cover contacting the wearer's head 660. In an embodiment the pre-loaded angle for the ear cover relative to the frame to provide twisting force is around 10 degrees.

In an embodiment the relative geometry of the frame and rotational mounting applies a twisting force. The frame is held in a relatively fixed position within the rotational part of the rotational mounting to limit relative movement between the frame and mounting perpendicular to the main axis of rotation of the rotational mounting. The frame and rotational mounting are configured such that at rest the ear cover is held at a pre-loaded angle, angled inwardly at the bottom of the ear cover. This can be achieved by having the ear contacting surface of the ear cover angled relative to the rotational mounting. For example, the rotational mounting may be a disc and pivot type mounting, with the frame end located within the disc to enable force from the frame to be distributed over the disc. The disc 620 is angled relative to the ear cover side 720 to cause the frame end to flex outwardly 710 when in position on the wearer's head. It should also be noted that the axis of rotation 810 of the rotational mounting is perpendicular to the disc and so will be angled toward the centre of the wearer's ear, rather than toward the top of the ear.

The frame provides a resilient skeleton and can be formed to have a curved band 850 to curve around the wearer's head and across their face, with relatively straight side edges 840 and an end portion 830 to engage with the rotational mounting 820. In the example shown in FIG. 8 the end portion 830 is configured to flex to provide the additional twisting force while the sides 840 remain relatively straight and parallel with the wearer's head for ease of movement between an eye covering position and positions either on top of the wearers head or below their chin. For example, materials having different resilient properties may be used in different portions of the frame. In another example, thickness and therefore resilient properties of the band or resilient skeleton may vary in different regions of the band or resilient skeleton. Alternatively, the frame may be formed with various to curves or elbows to control flexing and frame shape in the rest and worn positions. Other embodiments are envisaged.

Figure 8:
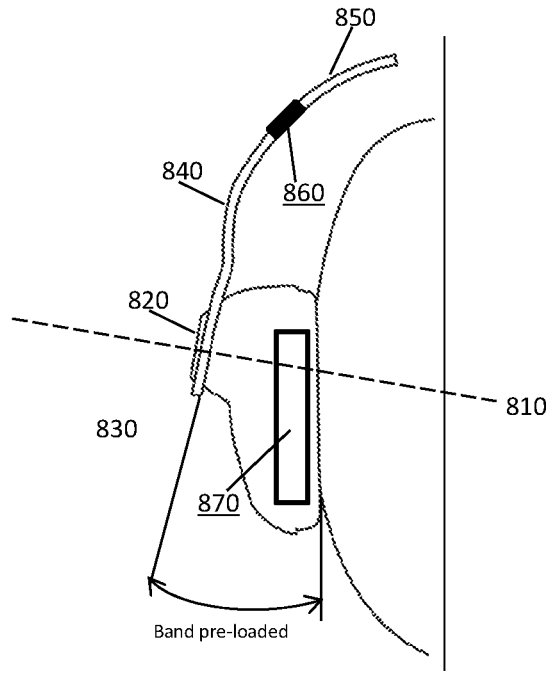
FIG. 8 illustrates frame flexing when worn in an overhead position with the ear cover mounted at a preloaded angle.
Figure 9:
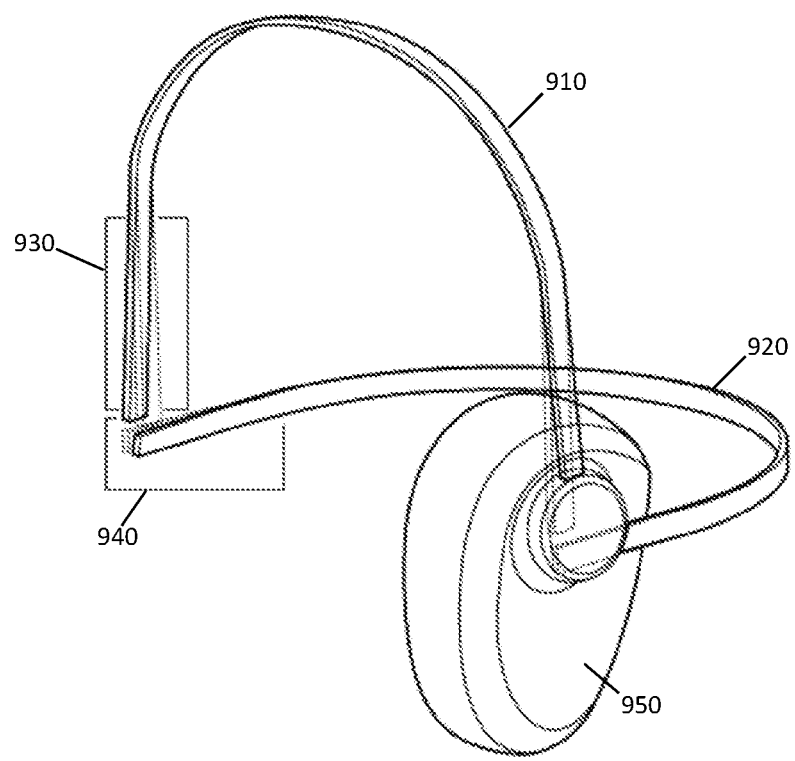
FIG. 9 represents the overhead and eye covering band positions.
Figure 10:
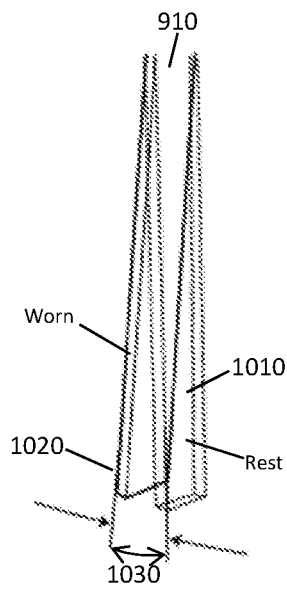
FIG. 10 comparatively illustrates at rest and worn frame end flexing when in an overhead position.

In an embodiment the twisting force is provided by the frame resilience, and angular orientation of left end portion and right end portion within the respective rotational mountings when worn. FIGS. 7 and 8 show the twisting force applied by the frame when in an overhead position. However, as represented in FIG. 9, the ear cover assembly is configured for the frame to move between at least an overhead position 910 and an eye covering position 920. Sections 930 and 940 are shown in more detail in FIGS. 10 and 11 to further illustrate the frame ends at rest and when worn in the overhead and eye covering positions respectively for an embodiment of the invention. FIG. 10 provides a comparative illustration of the frame end for the overhead position 930. As discussed above, in the overhead position, the end of the frame 910 will be straight at rest 1010 and flexed outwardly 1020 when worn. In this example, when the frame is overhead (vertical) when worn the band will flex by around 10 degrees to apply twisting force to the ear cover. The amount of outward flex 1030 and resilience of the frame material determining the amount of twisting force applied by the frame end to the ear cover 950.

Figure 11:
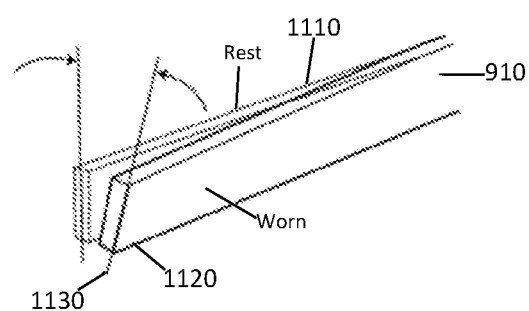
FIG. 11 comparatively illustrates at rest and worn frame end flexing when in an eye covering position (lowered position)

When in the eye covering position, with the frame horizontal, the twisting force still needs to be applied. To apply additional force to urge the lower portion of the ear covers inwardly and provide more even clamping force in the eye covering position, the frame is configured to also twist longitudinally (for example, 10 degree twist). As shown in FIG. 11, in the eye covering position longitudinal twisting of the frame in when worn 1120 relative to at rest 1110 can provide additional twisting force. In the worn position 1120 the end of the frame 910 is twisted longitudinally to cause the lower edge of the frame to be angled outwardly relative to the wearer's head. This twisting force can provide additional clamping force to the lower part of the ear cover.

It should be appreciated that any configuration of frame, ear cover and mounting that causes the frame resilience to apply a torsional force toward the lower edges of the ear cover can improve clamping over the ears for an offset mounting position. And any such configuration is contemplated within the scope of the present invention.

In an embodiment the relative geometry of the mounting and frame in combination with the frame resilience provides the torsional force for the frame in both overhead and eye covering positions. Embodiments can also enable an under chin position of the frame. In an embodiment each rotational mounting is configured to hold the respective frame end portion such that for any rotational orientation of the frame when worn, the lowermost part of the frame end portion retained within the mounting is angled outwardly relative to the uppermost part of the frame portion retained within the mounting to thereby cause the twisting force when worn. It should be appreciated that maintaining the lowest edge of the frame angled outwardly will cause the resilience of the frame to apply a twisting force urging the lower edge inward. With a relatively wide band having the rotational mounting angled relative to the ear cover side (as illustrated) in FIGS. 6 to 8 can also cause the frame to twist longitudinally when lowered to an eye covering position to apply additional twisting force.

A challenge is providing this twisting force with the frame in the eye covering position with a relatively narrow frame. A narrow frame can be desirable as this will typically require less material to manufacture, is less likely to limit vision, may be lighter, and may be more comfortable to wear. Further enabling a narrower frame may also allow more design options, both aesthetic and functional. For example, allowing a relatively narrow frame to act as a functional skeleton for decorative, fashionable design elements, such as a skeleton for aesthetic elements of sunglasses frames. A relatively narrow frame skeleton may be sufficiently light and strong to enable relatively heavy eye cover assemblies to be supported, for example protective face masks, heavy duty safety goggles or visors.

Figure 12:
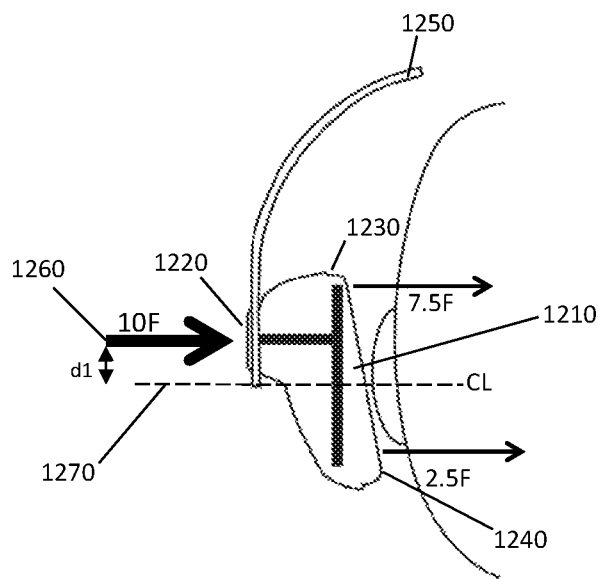
FIG. 12 illustrates an embodiment of an ear cover with the frame in an overhead position and at rest.
Figure 13:
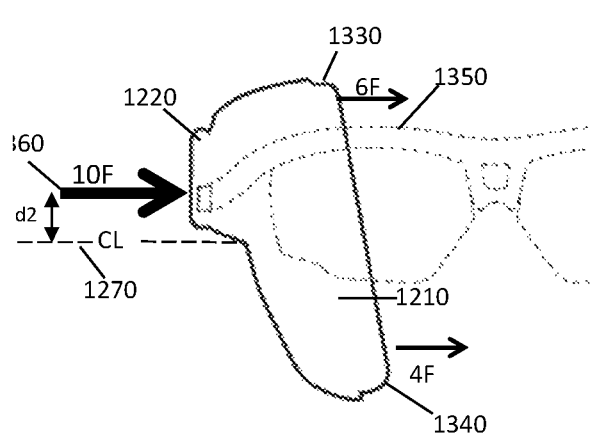
FIG. 13 illustrates the ear cover of FIG. 12 with the fame in a eye covering position and at rest.
Figure 14:
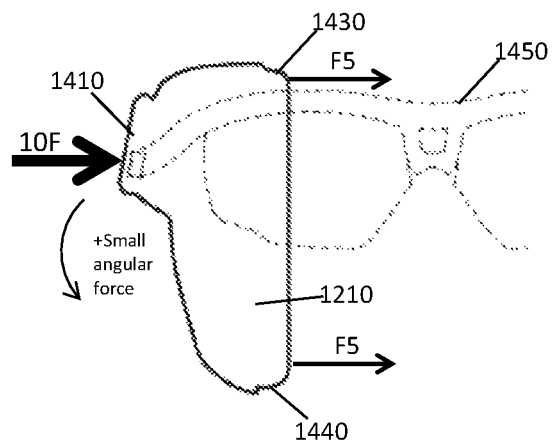
FIG. 14 illustrates the ear cover of FIG. 12 with the fame in a eye covering position and the ear cover in a worn position.
Figure 15:
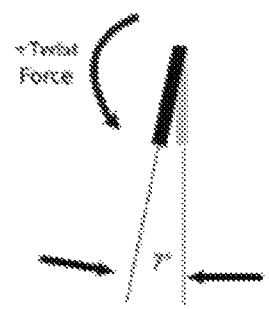
FIG. 15 illustrates the twist force applied by the frame in the eye covering position when worn.

In an embodiment the challenge of providing sufficient twisting force in the eye covering position with a relatively narrow frame is addressed by having the frame mounting position within the rotational mounting offset from the main axis of rotation toward the centre of the ear cover. This has the effect of reducing the distance between the ear cover centre and the frame clamping position when the frame is in the eye covering position. In turn, this reduces the difference in clamp force distribution between the upper and lower ends of the ear cover. This enables a lower additional twisting force to be required for more even clamping when the frame is in the eye covering position. This is explained in more detail with reference to FIGS. 12 to 15. FIG. 12 shows an ear cover 1210 attached to a frame 1250 using a rotational mounting 1220 with the frame 1250 in an overhead position and at rest with the ear cover 1210 angled inwardly at the bottom edge 1240 relative to the upper edge 1230. A clamping force 10 F applied at the axis of rotation 1260 of the mounting 1220 by the band 1250 (in this position without additional twist force) will be unevenly distributed, with a stronger clamp force at the top edge 1230 (7.5 F) than the bottom edge 1240 (2.5 F). The offset d1 between the force application point 1260 from the centre of the ear cover 1270 causes the uneven force distribution. As discussed above in an embodiment the frame is supported in the mounting offset from the pivot point so that in the eye covering position (horizontal) the frame is held below the axis of rotation of the mounting, closer to the centre of the ear cover. FIG. 13 illustrates the effect on force distribution when the point at which clamping force is applied 1360 is closer to the centre line 1270 of the ear cover 1210. In this example, where d2<d1, the difference between the distribution of clamping force by the frame 1350 (10 F) between the top edge 1330 (6 F) and bottom edge 1340 (4 F) of the ear cover 1210 is less. Thus, a smaller additional twisting force supplied via the frame twist in the eye covering position 1350 may be sufficient to hold the ear covers in place when worn. FIG. 14 shows the ear cover 1210 in the worn position with the frame 1450 end 1410 twisted to apply additional force to balance the offset (higher) mounting point. In this example a twist of around 7 degrees, as shown in FIG. 15 may be sufficient. It should be appreciated that due to the frame attachment point being below the rotational mounting axis, closer to the centre of the eye cover in the eye cover position, the load case for the ear covers is different between the overhead and eye cover frame positions. And a smaller twisting force can be used in the eye cover position. This enables less twist to be needed in the frame.

FIG. 16a shows an example of an embodiment where the channel 1610 for holding a frame 1650 end in a rotational mounting 1620 allows for difference in frame twisting angles as the frame 1650 moves between an overhead to eye covering position. FIG. 16b shows the section 1670 in more detail. In this embodiment the channel 1610 has angled walls to allow some movement of the frame within the channel but also limit the rotational movement so that the frame will engage with the walls to cause twisting of the frame. In this embodiment the walls are angled to allow only 3 degrees 1660 of movement of the frame 1650 within the channel 1610. Thus, where the relative angle of the mounting to the ear cover side is 10 degrees, with the frame in the eye cover position the relative angle between the ear cover and frame will reduce to 7 degrees as shown in FIG. 16a. It should be appreciated that other relative angles may be used in different embodiments and the geometry chosen may also depend on the resilience of the frame material.

FIGS. 17a and 17b show an embodiment of an ear cover and relative geometry of the rotational mount. The rotational mounting 1720 is oriented such that the plane of rotation 1725 is angled relative to plane 1715 through the ear contacting edges of the ear cover. The rotational mounting 1720 includes a channel 1730 for receiving the frame end portion 1750, the channel is offset from the main axis of rotation 1735 of the mounting 1720 in a direction toward the ear cover centre 1740. The frame end portion 1750 is configured to engage with one or more surfaces within the channel 1730. For a worn position where the ear cover 1710 is over the wearer's ear and the frame is lowered to the eye covering position (substantially horizontal) the channel 1730 will be substantially perpendicular to the meridian line 1760 through the ear cover as shown in FIG. 17b. The surfaces within the channel 1730 are configured such that in a rotational position where the channel is substantially perpendicular to the meridian line 1760 though the centre of the ear cover the surfaces cause longitudinal twisting of the frame end portion 1750 to cause the twisting force when worn. For the frame 1750 in the overhead position as shown previously in FIGS. 6 to 8, the channel 1730 will be substantially parallel to the meridian line 1760 through the centre of the ear cover and contact with the surfaces of the channel cause longitudinal flexing of the frame end portion due to the angle of the channel 1730 relative to the plane of the ear contacting edges 1715 to provide the twisting force when worn. It should be appreciated that the angle of the plane of rotation of the rotational mounting relative to the plane of the ear contacting edges and the offset channel will cause the lowermost part of the frame to be forced outwardly of wearer's head when the apparatus is worn, to cause twist force to be applied on the rotational mounting by the frame. This twist force applies additional force to the lower portion of the ear cover to compensate for the uneven clamp force due to the rotational mounting being located above the centre of the ear cover.

In an embodiment the frame ends are planar for engagement with the surfaces within the channel of the rotational mounting. However other embodiments are envisaged, for example in an embodiment the frame may be a wire having ends bent to engage with the channel surfaces. Alternatively, the frame ends may have a profile shaped to engage cooperatively with surfaces within the channel, for example having projections to engage with surfaces in the channel. In an embodiment the frame is a substantially planar band resilient, shaped to curve around the wearer's face and having planar ends for engaging with surfaces within the rotational mounting.

Figure 18:
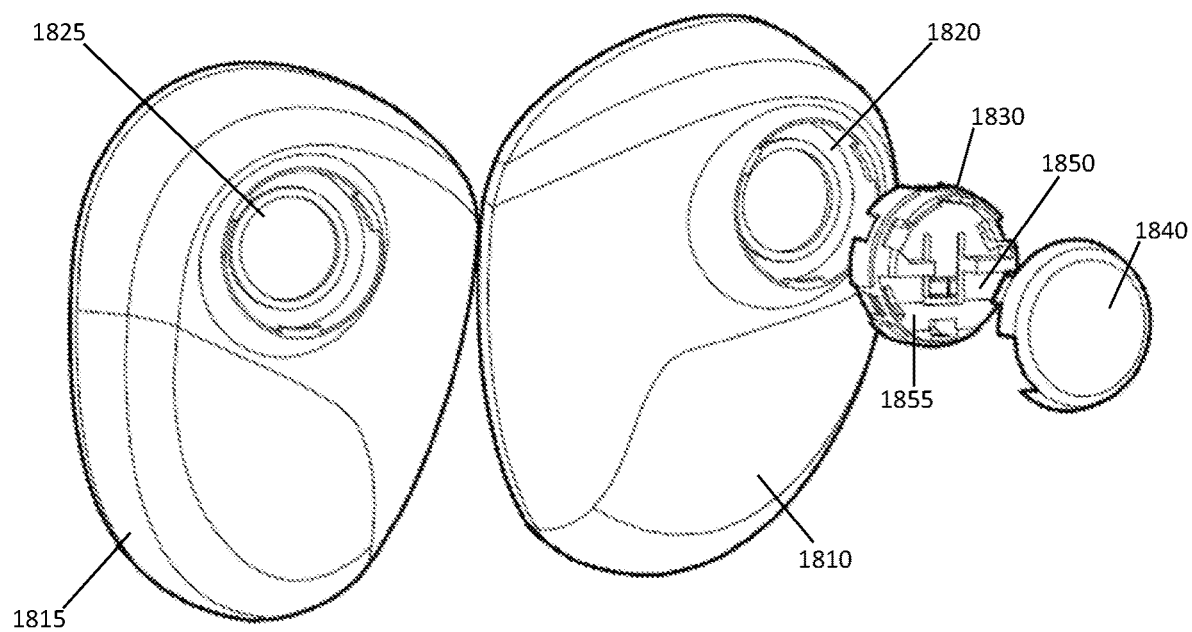
FIG. 18 illustrates an embodiment of the rotational mounting for asymmetrical ear covers.
Figure 19:
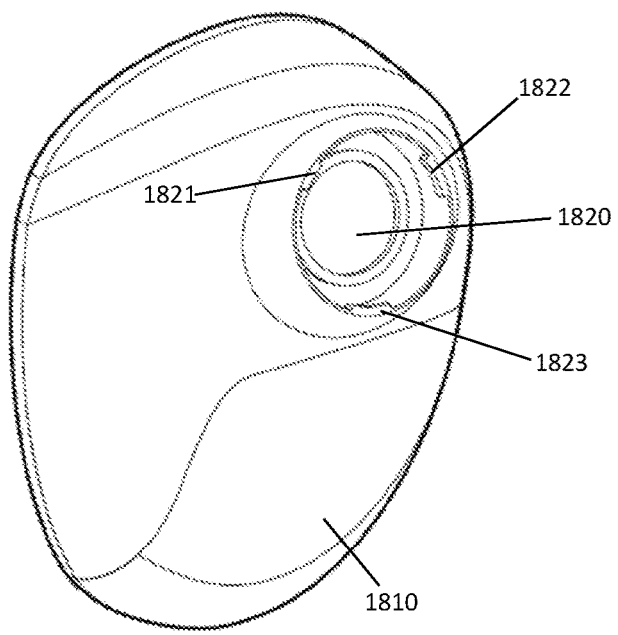
FIG. 19 shows a left ear cover.
Figure 20:
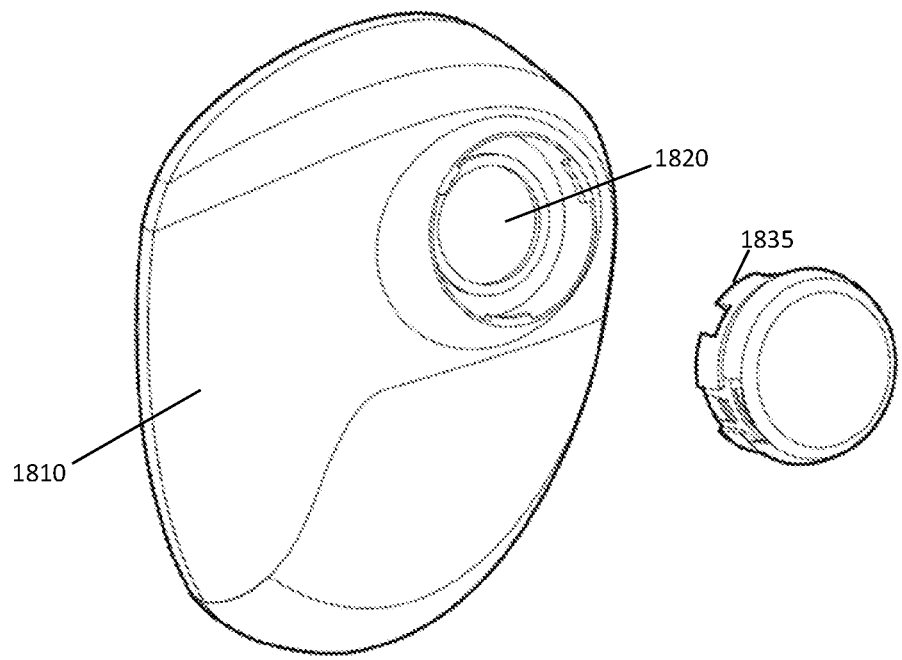
FIG. 20 shows the left ear cover and rotational mounting ready for assembly.

A preferred embodiment of an ear cover and rotational mounting assembly is illustrated in FIGS. 18 to 20. In this embodiment each ear cover 1810, 1815 comprises a rotational mounting socket 1820, 1825 in a fixed position in the upper portion of the ear cover 1810, 1815, and one or more rotational assembly components 1830, 1840 to be received in the socket to form a rotational plug including the channel 1850 for receiving the frame end. The socket 1820, 1825 is oriented such that the plane of rotation of the plug is angled relative to the plane of the ear contacting edges of the ear cover. In this embodiment the ear covers have a rigid outer shell in which the socket is formed. A rigid outer shell is typically used for safety equipment applications and for electronic headphones as the rigid outer shell can provide good sound insulating properties. However, other embodiments are also envisaged, for example a soft shell ear cover having rigid frame members for maintaining the relative orientation of the rotational mounting and ear cover edges as discussed above, such an embodiment may be suitable for an assembly having a pair of warming ear muffs and the frame forming sunglasses for wearing skiing or otherwise outdoors in cold and bright conditions.

It should be appreciated that for any embodiment once the ear cover apparatus is assembled the apparatus will have a left and right configuration due to the relative orientation between the respective ear covers and frame to provide the twisting. Also the eye cover assembly will typically have a portion shaped to rest on the bridge of the wearer's nose. The apparatus may be assembled using symmetrical ear covers with left and right configuration mountings, formed to provide the relative angled orientation for the ear covers once assembled. Alternatively, the ear covers may be asymmetrical.

In the embodiment shown in FIG. 18 the two ear covers are asymmetrical, and the ear cover apparatus comprise paired left and right ear covers. In this embodiment the left and right ear cover shells are asymmetrical due to the offset pivot position for the frame. The socket 1820, 1825 of each asymmetrical ear cover is oriented such that the plane of rotation of the plug of the rotational mounting is angled relative to the plane through the ear contacting edges allowing an identical plug to be used for assembling the rotational mounting for each of the left and right ear covers. In this embodiment the rotational mounting plug 1835 (shown assembled in FIG. 20 and also referred to as a pivot knuckle) comprises a main rotational plug component 1830 and a cover 1840. The main rotational plug component includes angled faces 1855 within the frame receiving channel 1850 to cause the frame angle to be adjusted and twist in the eye covering orientation as discussed above. The angle of the surfaces in the channel 2150 can also be seen in FIG. 21d. The main rotational plug component can be moulded in a self-lubricating acetal polymer. The main rotational plug can also be configured to use minimal points of contact with the socket to reduce surface friction between surfaces and provide ease of rotation. Embodiments can also include recesses and pockets to allow dust and debris that may gather in the pivot cavity to be distributed away from the rotating contact surfaces. This may be an optional feature as this is particularly advantageous for embodiments configured for use in harsh environments such as industrial or mining eye and ear safety apparatus. This feature may be less important for embodiments configured for urban use, such as for stereo headphones.

Figure 21A:
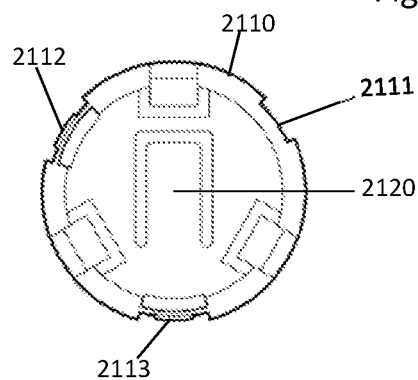
FIGS. 21a to 21d show various views of the main component of the rotational mounting the example of FIG. 18.
Figure 21B:
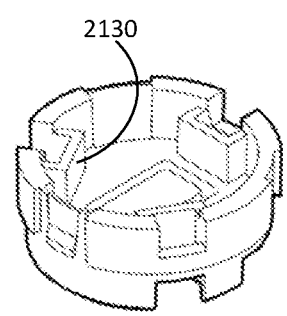
Figure 21C:
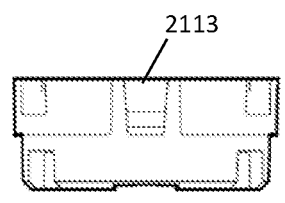
Figure 21D:
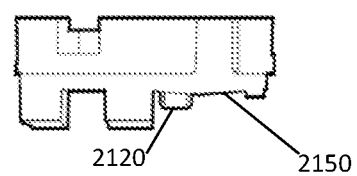

An embodiment of the main rotational component is shown in more detail in FIGS. 21a to 21d. FIG. 21a shows an underside of the main rotational plug component 2110. The main rotational plug component 2110 can include bayonet features 2111, 2112, 2113 for retention of rotational mounting plug in the socket which are also configured to orient the rotational mounting in the socket correctly for respective left or right operation. For example, the embodiment show uses a small bayonet entry lock feature 2111 to engage with a small lock component 1821 formed in the forward part of the socket 1820 (shown in FIG. 19) and two larger bayonet entry lock features 2112, 2113 to engage with larger lock components 1822, 1823 formed in the socket 1820. An external view of this snap lock feature 2113 is also shown in FIG. 21c. These socket lock components are configured in each socket to ensure the mounting has the appropriate orientation. This means that the same component can be used for either side with reduced possibility for errors during assembly.

Figure 22A:
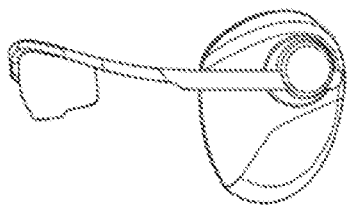
FIGS. 22a to 22c illustrate adjusting position of the ear cover along the end of the frame.
Figure 22B:
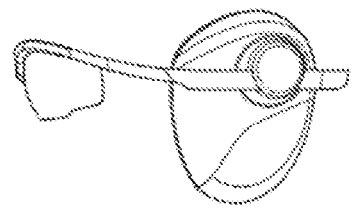
Figure 22C:
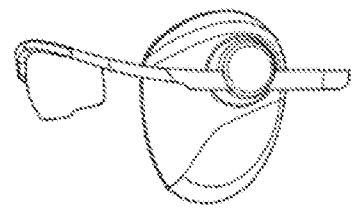

The main rotational component can also be configured to snap lock into the socket. In the embodiment shown the larger bayonet features 2112, 2113 include spring loaded snap locking features. The rotational mounting also includes features for locking the cap to the plug. The rotational mounting can also include a spring arm 2120 for a ratchet adjustment mechanism to enable adjustment of the position of the mounting along the end of the frame, for example to adjust for different head size and to enable the frame position to be adjusted, for example to rotate past the wearer's chin. FIGS. 22a to 22c illustrate different positions of the ear cover along the frame end.

This embodiment may have manufacturing advantages, such as ease of assembly by removing the need to ensure correct pairing of both left and right rotational mounting plugs and left and right ear covers. Enabling both left and right rotational mountings to utilise identical plug components may reduce manufacturing costs through reduction of parts. This may also be advantageous for managing spare parts and repairs.

The frame is an important component of the assembly, the resilience of the frame providing both clamping and twisting force to hold the ear covers in place. The frame comprises a central portion shaped to surround the wearer's head and orient the ear covers, and respective left and right end portions configured for engagement with the rotational mounting. The central portion is configured to support an eye cover assembly which can be any form of visor or eye protector. The frame can comprise a resilient skeleton spanning the right end portion, central portion and left end portion of the frame and providing resilience to apply the clamping force. For example, target clamping forces may be in the range of 8 to 18 newtons. Required clamping force may vary based on the nature and use of the article. For an embodiment used for safety goggles the target clamping range may be 10-12N whereas for headphones with blue-light filtering visors designed to be worn while a person is substantially stationary may require a lower clamping force such as 6-8 newtons. Articles configured for active sports, mining or emergency services may require higher clamping forces.

In an embodiment the resilient skeleton is an elongate curved band and being substantially flat through the left end portion and right end portion. The band can be formed of resilient metal. Alternatively, the band may have a composite construction comprising one or more layers of material. The material may be joined or laminated to provide resilient properties. In an embodiment the band has a composite structure comprising one or more layers of resilient material in a laminate structure.

In some embodiments the frame or a frame skeleton may be formed of or include plastic material having requisite stiffness and resilience to satisfy the functional requirements for the frame. Materials which may be suitable for some embodiments include, but are not limited to polyoxymethylene (POM), or polyester and polycarbonate blended plastics such as polycarbonate and polybutylene terephthalate (PC/PBT or PC+PBT) or polycarbonate and polyethelene terephthalate (PC/PET or PC-FPET). However, any material of sufficient strength, stiffness and resilience may be used. For example, flexural strength within the range of 60-100 MPa. It is desirable to keep maximum stress in localised regions of the frame below 50% of the flexural strength. As the frame material will be subject to high stress levels for extended periods of time, while the article is being worn, exceeding half the flexural strength of material is not recommended. If stress exceeds half the flexural strength then the material will potentially weaken over time, which may lead to stress fractures or fatigue failures in the frame.

Figure 2A:
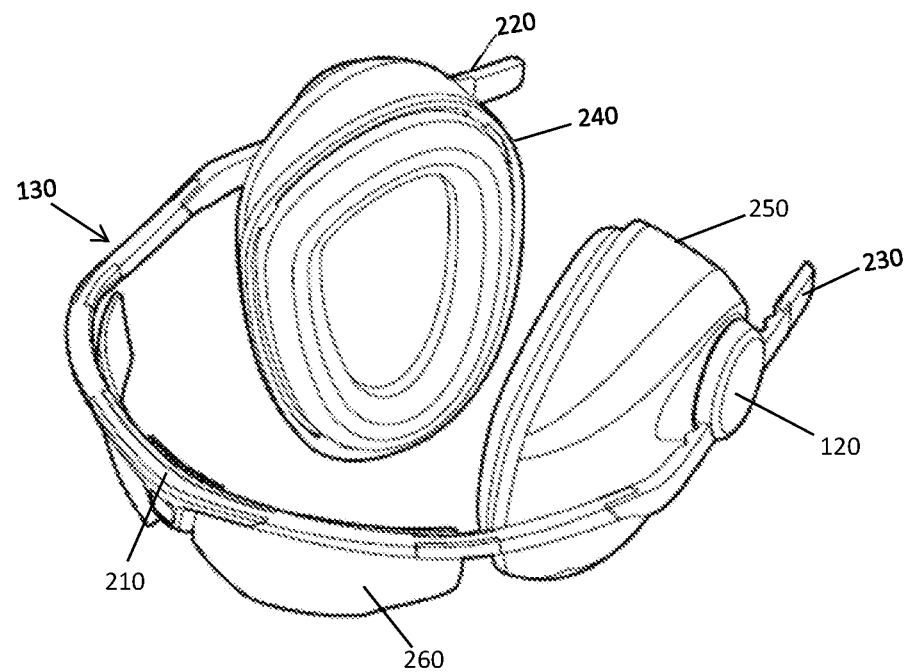
FIGS. 2a to 2d show the device of FIG. 1 from different angles.
Figure 2B:
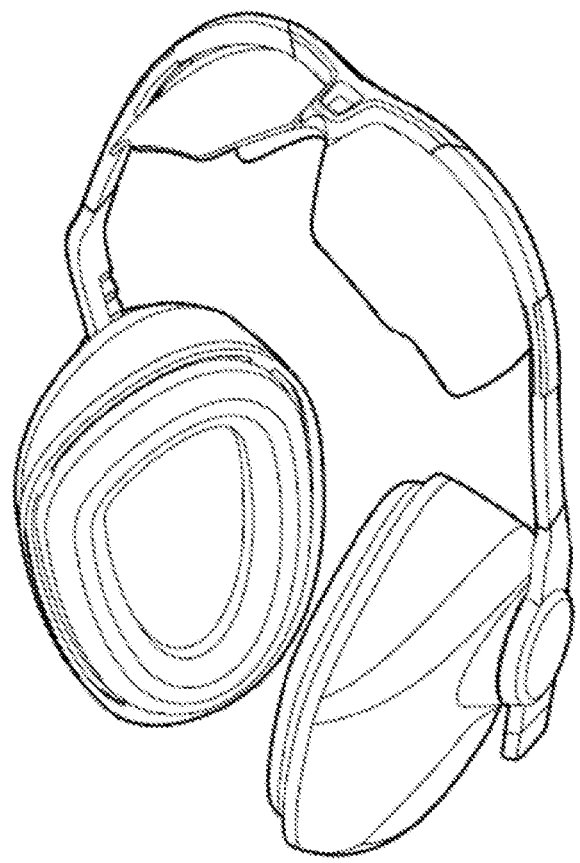
Figure 2C:
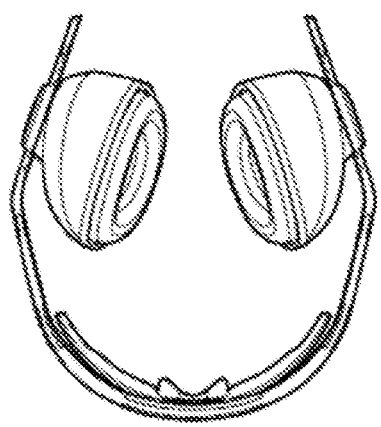
Figure 2D:
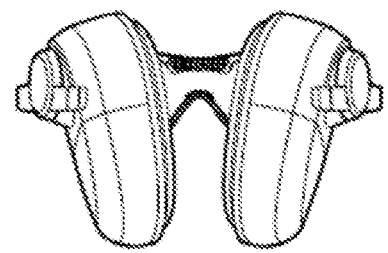

In the safety glasses example embodiment illustrated in FIGS. 2a-c, to achieve good operational results the frame should be designed to exert a target frame force between preferably of 10-12 N through the frame arms when extended from a rest separation width arms at an extended from a resting width of 114 mm to an extended with of 255 mm, with a maximum extension limit of 300 mm.

In an embodiment the band has a non-metallic coating. For example, for applications where exposed metal is undesirable or prohibited the frame may be a metallic frame with a polymer coating. In an example, Australian safety regulations for mining operations do not permit safety apparatus to have any exposed metal. For such applications if the frame comprises a resilient metal band then this can be encased in plastic or another non-metallic coating.

In an embodiment the coating can contribute to the resilient properties of the frame. The non-metallic coating can increase the resilience of the frame. For example, for a metaling band style frame adding a plastic coating can increase the stiffness of the frame and there increase the claiming and twisting force that may be applied by the frame. For example, where using a plastic coating the thickness and/or hardness of the plastic coating can affect the overall frame stiffness. The type of material coating may be chosen based on target band properties, and may also be based on the target application for the device. In an embodiment different coatings may be used in different areas of the frame to alter the resilient properties over the length of the frame. For example, a substantially rigid or rigid plastic coating may be used in a region of the frame where an eye cover assembly is mounted. This may be desirable to limit or prevent transfer of flexing of the frame to the eye cover assembly. For example, for safety glasses, the frame may include a non-resilient eye cover assembly mounting configured to mount an eye cover assembly to the central portion.

The eye cover assembly for a safety application may include be configured as safety glasses, a safety visor or mask. An embodiment can include a ballistic protective the eye assembly. In another embodiment the eye cover assembly can be configured as sunglasses.

In another embodiment the eye cover assembly may comprise a visor or lenses configured to relive eye strain, for example the visor or lenses including material or coatings to filters some light wavelengths associated with eye strain. In an example the eye cover assembly may be configured as gaming glasses, configured relieve eye strain by filtering some "blue light" wavelengths associated with eye fatigue. Gaming glasses eye assembly embodiments can also be configured for enhancing game play experiences, such as any one or more of polarisation, enabling three dimensional effects, reducing screen glare, enhancing image colour and contrast. In another embodiment the eye cover assembly can include a virtual reality visor or goggles, optical head mounted display, camera, wearable computer glasses (smart glasses) etc.

In embodiments of the eye cover assembly can also include optical devices such as night vision goggles or binoculars.

In an embodiment a camera may also be mounted in an ear cover. For example, a camera may be mounted in a lower portion of the ear cover so as to be directed where a wearer is facing. This may also minimise likelihood of obstruction by the frame or other headwear, for example if a wearer lowers the eye cover this will typically be to below the chin, whereas partial lowering that may obstruct the camera would likely also obstruct the wearer's vision or lower face. Using ear cover mounted cameras can avoid needing the eye cover assembly to be in place for the camera to be focused forward, as the ear covers will typically remain in place on the wearer's ears while the frame position may be often changed. A camera may be mounted in each ear cover for improved field of view. For example, ear cover mounted cameras may have a portion of the field of view obstructed by the wearer's face, and this may be compensated for by using a camera in each ear cover.

In some embodiments the eye cover assembly is configured to include vision corrective lenses. The eye cover assembly may be configured to enable removable attachment of vision corrective lenses. For example, the frame may include apertures or pockets to enable for insertion of vision corrective lenses. Alternatively, the vision correctly lenses may be attached to a visor that can be mounted on the frame, the visor may be removable. Alternatively, the visor may be fixed to the frame and the ear covers removably attached to the ear protectors. For example, an assembly kit may include a frame with a sunglass visor and a frame with a safety glass visor and a pair of ear covers attachable to either frame. The eye cover assembly can include integrated vision corrective lenses. The eye cover assembly can also be removably attached to the frame.

The ear cover assembly can be configured to allow adjustment of the position of each ear cover along the respective left end portion or right end portion. For example, the mounting can be configured to enable the ear cover to slide along the frame as shown in FIGS. 22*a* to 22*c*. In an embodiment the rotational mounting is configured with a channel to allow sliding of the rotational mounting along the respective frame end portion. In an embodiment the frame end portions include a ratchet portion and the rotational mounting is configured to engage with the ratchet portion to inhibit unintentional sliding of the rotational mounting along the frame end. For example, the rotational mounting plug shown in FIG. 21*a* includes a ratchet adjustment spring to engage with a ratchet portion on the frame end to inhibit unintentional movement along the frame end.

In an alternative embodiment surface friction between the rotational mounting and the respective frame end portion inhibits unintentional sliding of the rotational mounting along the respective frame end.

The ear covers can be ear muffs style ear protectors configured to provide hearing protection for the wearer. In an embodiment each ear protector comprises an inner sound insulating portion adapted to rest against and substantially or entirely cover the outer ear of a wearer; and an outer shell made of rigid material and attached to the inner insulating portion, wherein the rotational mounting is attached to the outer shell of the ear protector. In an embodiment the rotational mounting socket is formed in the rigid outer shell. The shell may include a removable portion adapted to be selectively removed and replaced. For example, this may enable sound insulating qualities of the ear protector to be adjusted by adding or removing additional sound insulating material via the aperture in the outer shell.

In another embodiment at least one ear cover includes an electronic device 870 comprising a receiver and speaker. The receiver and speaker may be wired or wirelessly connected to a device such as a mobile phone, radio, music player, computer, mixing desk etc. The receiver may be a wireless, for example FM, AM, DAB receiver. The receiver may also be wireless transceiver, for example WiFi, Bluetooth, two way radio receiver etc. For example, an ear cover may include Bluetooth hands-free communication device for use with devices such as a mobile phone, computer or music player. Alternatively, the ear covers may include a two way radio.

Embodiments can also include a microphone extending from one of the eye covers. The microphone may be part of a two way radio or telecommunication apparatus. Alternatively, the microphone may be linked with a computer system or other device via a wired or wireless connection. Embodiments having a microphone may have at least one ear cover incorporating a speaker. In an embodiment the assembly includes headphones and a microphone 860. In an embodiment the assembly includes stereo headphones, a microphone 860 and eye assembly configured for gaming. In an alternative embodiment the assembly can be configured for use in industrial, law enforcement, protective services, firefighting or military applications and comprise wireless two way communication devices in the ear covers and microphone. In an example the microphone is attached to an ear cover, for example on a stem attached to the ear cover via a fixed or adjustable mounting, the stem being configured to support the microphone proximate the wearer's mouth when worn. The stem mounting may be a second rotational mounting enabling the microphone position relative the wearer's mount be adjusted without disturbing the ear cover. In another embodiment the microphone is embedded in an ear cover.

In an alternative embodiment the frame 850 of the ear cover assembly is not used to support an eye cover assembly, instead the frame may support a device to be worn proximate a wearer's mouth, such as a microphone 860 or mask. Such embodiments may be used where an eye cover is not necessary, for example for telephony or computer headsets for receptionists, gaming, dispatch operators, call centre workers, office workers, salespersons, floor managers, security personnel, sports coaches/trainers, radio journalists, film/video production crews, sports commentators, stage managers, pilots, rally/racing car drivers, construction equipment operators, site managers etc. Embodiments can use wired or wireless communication protocols. The configuration of the assembly may vary depending intended use.

For example, a headset made for indoor office use may be lightweight with the frame designed with aesthetics and comfort as a priority, as the expectation would be that the wearer is relatively still or only involved in low impact movement while wearing the device so the resilience needed to maintain the device in place may be substantially less than for a device designed for wearing by a rally car driver or security personnel. A device designed for office type use may also include only one ear cover, for example the frame may attach to an ear cover on one side via a rotational mounting and on the other side be rotatably mounted to a pad or bar to rest against the wearer's head.

In embodiments for industrial, military, law enforcement, firefighters, sports etc. may have stronger frames designed to provide stronger clamping an torsional forces to reduce the likelihood of the device being dislodged in use.

It should be appreciated that the rotational mounting may be offset to be below the centre of the ear cover where the frame supports a microphone 860 or other such device. The geometry between the rotational mounting and the frame can be configured to cause frame twist to distribute clamping force over the ear cover, the twisting force acting to increase clamping force applied to the upper part of the ear cover. Having a lower rotational mounting point may be advantageous for some applications, for example for military, motorsports, riggers or pilots where the device may be worn with a variety of helmets. A lower rotational mounting point allows the top of the ear cover to have a thinner profile which may be less prone to interfering with some types of headwear.

In some embodiments the rotational mounting may be centrally located with the relative geometry of the frame and rotational mounting configured to adjust the amount of clamping force applied by the frame twist at different rotational positions. For example for an ear cover assembly mounting a microphone 860 for office worker type use, the relative geometry may be configured to apply increased clamping force when the frame is rotated such that the microphone is proximate the wearer's mouth and apply reduced clamping pressure when the frame is in a rest position below the chin, thus enabling the wearer to reduce the pressure applied when the microphone is not in use allowing the device to be worn more comfortable for long periods of time. Many workplaces have open plan working environments and within such environments background noise can be a problem for some people. Wearing headphones with nose cancelling electronics (even without listening to music or being on the phone) is one strategy that can be utilised to reduce background noise distractions. By enabling the clamping force to be reduced when the microphone 860 is in a rest position may enable a person to more comfortably wear the device for a long period of time. Particularly for embodiments where the ear covers include noise cancelling electronics the ability to reduce the clamping pressure may make the device more tolerable to wear for long periods of time. It should be appreciated that not needing to have a band over the head may also be an advantage for some individuals for reduced interference with hair styles or headwear.

In alternative embodiments the frame of the ear cover assembly may support both a microphone and eye cover. Other devices may also be incorporated into the frame such as cameras, sensors, head up displays etc. In such an embodiment one or more device may be integrated with the eye cover—for example as smart glasses. Alternatively, or additionally the frame may be provided with additional mountings for devices.

In an embodiment the ear covers are configured as a pair of headphones. In an example the ear covers may be stereo headphones. For example, the ear covers may have wireless Bluetooth or WiFi receivers for listening to music from a mobile phone or music player. For such an embodiment the eye cover may be sunglasses or vison corrective glasses.

In some embodiments the eye cover assembly can have some vision correction properties, for example the eye cover assembly can be configured to enable prescription lenses to be built into the device. The eye cover assembly can also be tinted and/or polarised to provide sun and glare protection.

It is a known problem with muff style ear covers is that the soundproofing seal between the ear cover and the wearer's head is broken when worn with safety glasses or spectacles. The arm of the glasses pushes the ear muff away from the wearer's head, sometimes causing a significant gap. This will reduce the sound protection provided to the wearer. This is a known problem with all ear muff style ear protectors currently available on the market. Further the ear muffs pressing safety glasses or safety goggle arms into the wearer's head can be uncomfortable. The level of discomfort can also increase over time. This is not only a problem for safety equipment but also for wearing headphones, for example for listening to music, with sunglasses or spectacles. Embodiments of the present invention provide a solution to this problem by enabling a combined ear cover and sys cover device of varying configurations.

It will be understood to persons skilled in the art of the invention that many modifications may be made without departing from the spirit and scope of the invention.

In the claims which follow and in the preceding description, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art, in Australia or any other country.

What is claimed is:

1. An ear cover assembly comprising:
two ear covers, each ear cover having a rotatable mounting located in a mounting position offset from a center of the respective ear cover;
a resilient frame comprising a right end portion, a central portion, and a left end portion,
each of the right end portion and the left end portion being configured to attach to a respective one of the ear covers via the respective rotatable mounting,
the central portion being configured to orient the right end portion and the left end portion to hold the ear covers opposite one another for placement in use to cover a wearer's ears, and to support an assembly for positioning in front of the wearer's face,
the resilient frame being configured to apply clamping force to urge the ear covers inwardly to hold the assembly in place on the wearer's head;
each rotatable mounting being configured to limit relative movement between the respective frame end portion and respective one of the ear covers in a direction perpendicular to a main axis of rotation of the rotatable mounting, and
the relative geometry of the frame and each rotatable mounting being configured to provide a twisting force to distribute the clamping force over the respective one of the ear covers to compensate for the offset mounting position, wherein the twisting force is provided by the frame resilience, and angular orientation of the left end portion and the right end portion within the respective rotatable mounting causing twist in the frame when worn to provide the twisting force, wherein each respective rotatable mounting is shaped to hold the respective left end portion and right end portion such that for any rotational orientation the respective left end portion and right end portion retained within the rotatable mounting is angled relative to the center of the respective ear cover such that a most central part of the respective left end portion and right end portion is angled outwardly of center of the respective ear cover relative to a least central part of the respective left end portion and right end portion retained within the rotatable mounting to thereby cause the twisting force when worn.

2. The ear cover assembly as claimed in claim 1, wherein the relative geometry of the frame and rotatable mountings being configured to alter the clamping force applied by the frame based on the rotational position of the frame.

3. The ear cover assembly as claimed in claim 2, wherein each rotatable mounting is oriented such that the plane of rotation is angled relative to a plane through ear contacting surfaces of the respective ear cover and includes a channel for receiving the respective left end portion and right end portion, the channel being offset from the main axis of rotation of the mounting in a direction toward the center of the respective ear cover, wherein the left end portion and the right end portion are configured to engage with one or more surfaces within the channel, the surfaces within the channel being configured such that in a rotational position where the channel is substantially perpendicular to a meridian line though the center of the respective ear cover, the surfaces cause longitudinal twisting of the respective end portion to cause the twisting force when worn, and in a rotation position where the channel is substantially parallel to the meridian line through the center of the respective ear cover, the surfaces cause longitudinal flexing of the respective left end portion and right end portion due to the angle of the channel relative to the plane through ear contacting surfaces of the respective ear cover to provide the twisting force when worn, and wherein the rotatable mounting for each ear cover comprises a rotational mounting socket in a fixed position in the upper portion of the ear cover, and one or more rotational assembly components to be received in the socket to form a rotational plug including the channel, and wherein the socket is oriented such that the plane of rotation of the rotational plug is angled relative to a plane through ear contacting surfaces of the respective ear cover.

4. The ear cover assembly as claimed claim 1, wherein the assembly supported by the frame is an eye cover assembly.

5. The ear cover assembly as claimed in claim 1, wherein the assembly supported by the frame is a microphone.

6. The ear cover assembly as claimed in claim 1, wherein the frame comprises a resilient skeleton spanning the right end portion, the central portion and the left end portion of the frame and providing resilience to apply the clamping force.

7. The ear cover assembly as claimed in claim 6, wherein the resilient skeleton is an elongate curved band and the band is formed of resilient metal.

8. The ear cover assembly as claimed in claim 6, wherein the resilient skeleton is an elongate curved band and the band has a composite structure comprising one or more layers of resilient material in a laminate structure.

9. The ear cover assembly as claimed in claim 6, wherein the resilient skeleton is an elongate curved band formed of plastic material.

10. The ear cover assembly as claimed in claim 6, wherein the frame further comprises a non-resilient eye cover assembly mounting configured to mount an eye cover assembly to the central portion.

11. The ear cover assembly as claimed in claim 1, further configured to allow adjustment of the position of each ear cover along the respective left end portion or right end portion.

12. The ear cover assembly as claimed in claim 1, wherein the ear covers are ear muffs style ear protectors configured to provide hearing protection for the wearer, wherein each ear protector comprises an inner sound insulating portion adapted to rest against and substantially or entirely cover the outer ear of the wearer; and an outer shell made of rigid material and attached to the inner insulating portion, wherein the rotatable mounting is attached to the outer shell of the ear protectors.

13. The ear cover assembly as claimed in claim 1, wherein at least one ear cover includes an electronic device comprising a wireless receiver and speaker.

14. The ear cover assembly as claimed in claim 13, further comprising a microphone assembly.

15. The ear cover assembly as claimed in claim 1, further comprising an eye cover assembly wherein the eye cover assembly comprises an eye protection assembly.

16. The ear cover assembly as claimed in claim 15, where the eye protection assembly is configured as any one of safety glasses, safety visor or mask.

17. The ear cover assembly as claimed in claim 15, wherein the eye cover assembly is configured for sunglasses.

18. The ear cover assembly as claimed in claim 15, wherein the eye cover assembly is configured to include vision corrective lenses.

19. An ear cover assembly comprising:
two headphone ear covers, each ear cover having a rotatable mounting;
a resilient frame comprising a right end portion, a central portion, and a left end portion,
   each of the right end portion and the left end portion being configured to attach to a respective one of the ear covers via its rotatable mounting,
   the central portion being configured to orient the right end portion and the left end portion to hold the ear covers opposite one another for placement in use to cover a wearer's ears, and to optionally support an assembly for positioning in front of the wearer's face,
   the resilient frame being configured to apply clamping force to urge the ear covers inwardly to hold the assembly in place on the wearer's head;
each rotatable mounting being configured to limit relative movement between the respective frame end portion and respective one of the ear covers in a direction perpendicular to a main axis of rotation of the rotatable mounting, and
the relative geometry of the frame and the rotatable mounting being configured to alter the clamping force applied by the frame based on the rotational position of the frame,
wherein an angular orientation of the left end portion and the right end portion within the respective rotatable mounting causes twist in the frame when worn, wherein each respective rotatable mounting is shaped to hold the respective left end portion and right end portion such that for any rotational orientation the respective left end portion and right end portion retained within the rotatable mounting is angled relative to a center of the respective ear cover such that a most central part of the respective left end portion and right end portion is angled outwardly of the center of the respective ear cover relative to a least central part of the respective left end portion and right end portion retained within the rotatable mounting to thereby cause the twist, and each rotatable mounting's respective plane of rotation of is angled relative to a plane through ear contacting surfaces of the respective ear cover to cause variation in degree of twist of the respective left end portion and right end portion retained within the rotatable mounting with varying rotational position of the frame to cause variation in the clamping force based on the rotational position of the frame.

20. An ear cover assembly comprising:

one ear cover having a rotatable mounting;

a head contacting support having a rotatable mounting; and a resilient frame comprising a right end portion, a central portion, and a left end portion, each of the right end portion and the left end portion being configured to attach to one of the ear cover via its rotatable mounting or the head contacting support via its rotatable mounting, the central portion being configured to orient the right end portion and the left end portion to hold the ear cover and the head contacting support substantially opposite one another for placement in use with the ear covering one of a wearer's ears and with the head contacting support against the wearer's head near their other ear, and to support an assembly for positioning in front of the wearer's face, the resilient frame being configured to apply clamping force to urge the ear cover and the head contacting support inwardly to hold the assembly in place on the wearer's head;

each rotatable mounting being configured to limit relative movement between the respective frame end portion and the ear cover or the head contacting support in a direction perpendicular to a main axis of rotation of the rotatable mounting, and the relative geometry of the frame and rotatable mounting being configured to alter the clamping force applied by the frame based on the rotational position of the frame, wherein an angular orientation of the left end portion and the right end portion within the rotatable mounting cases twist in the frame when worn, wherein each rotatable mounting is shaped to hold the respective left end portion and right end portion such that for any rotational orientation the respective left end portion and right end portion retained within the rotatable mounting is angled relative to a center of the respective ear cover or head contacting support such that a most central part of the respective left end portion and right end portion is angled outwardly of center of the respective ear cover or the head contacting relative to a least central part of the respective left end portion and right end portion retained within the rotatable mounting to thereby cause the twist, and each rotatable mounting's respective plane of rotation is angled relative to a plane through ear contacting surfaces of the respective ear cover or head contacting support to cause variation in degree of twist of the respective left end portion and right end portion retained within the rotatable mounting with varying rotational position of the frame to cause variation in the clamping force based on the rotational position of the frame.

\* \* \* \* \*